United States Patent [19]

Orth et al.

[11] Patent Number: 5,149,886
[45] Date of Patent: Sep. 22, 1992

[54] PREPARATION OF 9,9-BIS-(4-HYDROXYPHENYL)-FLUORENE

[75] Inventors: Winfried Orth, Hassloch/Pfalz; Emmerich Pastorek, Hemsbach; Wolfgang Weiss, Neckarhausen; Hans W. Kleffner, Battenberg/Pfalz, all of Fed. Rep. of Germany

[73] Assignee: Rutgerswerke AG, Fed. Rep. of Germany

[21] Appl. No.: 834,897

[22] Filed: Feb. 11, 1992

[30] Foreign Application Priority Data

Mar. 7, 1991 [DE] Fed. Rep. of Germany ....... 4107242

[51] Int. Cl.$^5$ .................. C07C 37/20; C07C 39/12
[52] U.S. Cl. .................... 568/727; 568/719; 568/720; 568/722; 568/724
[58] Field of Search .............. 568/719, 720, 718, 724, 568/722, 727

[56] References Cited

U.S. PATENT DOCUMENTS

| | | | |
|---|---|---|---|
| 4,024,194 | 5/1977 | Corn, Jr. | 568/719 |
| 4,049,721 | 9/1977 | Corn, Jr. et al. | 568/719 |
| 4,675,458 | 6/1987 | Riemann et al. | 568/727 |

FOREIGN PATENT DOCUMENTS 0180133 5/1986 European Pat. Off. ............ 568/727

*Primary Examiner*—Werren B. Lone
*Attorney, Agent, or Firm*—Bierman and Muserlian

[57] ABSTRACT

In a process for the preparation of 9,9-bis-(4-hydroxyphenyl)-fluorene by condensing fluorenone and phenol in a molar ratio of 1:4 to 1:8 at 30° to 90° C. in the presence of gaseous hydrogen chloride and β-mercapto-propionic acid catalyst, the improvement comprising distilling water of reaction and dissolved hydrochloric acid from the completed reaction mixture, dissolving the distillation residue in a nitrile, separating the crystallized adduct of nitrile and 9,9-bis-(4-hydroxphenyl)-fluorene from the nitrile and optionally dissociating the adduct to recover high purity 9,9-bis-(4-hydroxphenyl)-fluorene.

9 Claims, No Drawings

PREPARATION OF 9,9-BIS-(4-HYDROXYPHENYL)-FLUORENE

STATE OF THE ART

In the plastics industry, such bisphenols are used on a large scale in polycondensation processes, particularly as monomers. The products made from them are polyester resins and plastics with especially good heat-resistance properties which can be used for insulation of electrical conductors or for highly thermostable coatings. However, plastics with these advantageous properties can be obtained only if especially pure bisphenols are used for their production.

In accordance with the economic importance, therefore, numerous attempts at improving known synthesis methods and purifying the reaction products have been made. Playing a central role in this connection is the process of U.S. Pat. No. 3,546,165 by which nearly all later processes were inspired. According to it, fluorenone and phenol are used in the condensation reaction in a molar ratio of 1:4 so that the phenol functions during the reaction both as reagent and as solvent. The reaction itself proceeds in the presence of β-mercaptopropionic acid or mercaptoacetic acid with introduction of dry HCl gas at a temperature between 140° and 150° C. The high temperatures are necessary at this mixture ratio of the reagents so that the composition will remain stirrable. But, as later experiments have shown, they lead to the formation of undesired by-products.

The dilution with water or the steam distillation proposed by Morgan after the condensation reaction is unsuitable for processing the reaction mixture on an industrial scale. Although upon dilution with water, a white compound actually forms, it is compact, sticky, and no longer manageable in larger quantities. By steam distillation, too, the same sticky compound is obtained. Besides, evidently an additional discoloration of the reaction product is brought about by the treatment with hot water, and crystallization of the product is prevented.

According to Morgan's description, the separated product is dissolved in an alkaline solution and then precipitated by dropwise addition of hydrochloric acid. After recrystallization from toluene, 9,9-bis-(4-hydroxphenyl)-fluorene is obtained as a white crystalline product having a melting point of 224° to 225° C. in a yield of 46 to 56% of the theory. However, applicants, attempts to dissolve the above described white compound in alkaline solution proved costly and lengthy.

Later processes, therefore, aimed on the one hand to increase the yield, and on the other, to simplify the processing. To increase the yield, in the course of time a variety of catalysts usable in the process were tried. They included ionizable sulfur compounds such as sulfur monochloride, hydrogen sulfide, a variety of mercapto compounds or alkali metal sulfides which react with acids with formation of hydrogen sulfide. Also Friedel-Crafts catalysts were used such as $ZnCl_2$, $CaCl_2$, $AlCl_3$ or $SnCl_4$, which are active in the presence of HCl.

It was found, however, that not only the choice of catalyst has a determining effect on the yield and on the product quality, but so does particularly the reaction temperature and the molar ratio of the reagents. High yields could therefore be achieved both with Friedel-Crafts catalysts and with the mercaptopropionic acid described by Morgan if the reaction temperature was kept below 100° C., more particularly between 30° and 90° C., and if phenol was used in a fourfold to eightfold molar quantity based on the fluorenone.

In this temperature range, the condensation reaction in the process described in DE-OS 34 29 484 is carried out also. Fluorenone and phenol are reacted in the molar ratio of 1:4 to 1:6 in the presence of β-mercapto-propionic acid and concentrated sulfuric acid. By the subsequent workup, a crude yield of about 97 to 98% is obtained according to the patent. This, however, still includes a high proportion of undesired by-products, formed by dimerization and substitution. The further processing occurs in that, after the completed condensation reaction, methanol is added and only then poured into cold water and here, too, the oily compound separates. The supernatant, aqueous methanol-sulfuric acid-phenol solution, is separated and the residue is washed twice with water and neutralized with ammonium carbonate solution. Phenol still adhering is removed by repeated boiling with water. After drying and a second crystallization from isopropyl alcohol, a product having a melting point of 223° C. is obtained.

This process, however, has major disadvantages. In the processing of the reaction product, very large amounts of water contaminated with phenol and sulfuric acid occur which must be given special treatment under the clean water regulations. Besides, the lumpy crude product obtained in this process after the addition of water is difficult to handle. It filters poorly and is difficult to wash and neutralize for further purification.

OBJECTS OF THE INVENTION

It is an object of the invention to provide an inexpensive, easily performable process for the production of 9,9-bis-(4-hydroxyphenyl)-fluorene in high yield and purity, which makes it possible to separate in a simple manner the solvents used for product purification so that, if desired, they can be re-used in the process.

This and other objects and advantages of the invention will become obvious from the following detailed description.

THE INVENTION

In the novel process of the invention for the preparation of 9,9-bis-(4-hydroxphenyl)-fluorene by condensing fluorenone and phenol in a molar ratio of 1:4 to 1:8 at 30° to 90° C. in the presence of gaseous hydrogen chloride and β-mercapto-propionic acid catalyst, the improvement comprising distilling water of reaction and dissolved hydrochloric acid from the completed reaction mixture, dissolving the distillation residue in a nitrile, separating the crystallized adduct of nitrile and 9,9-bis-(4-hydroxphenyl)-fluorene from the nitrile and optionally dissociating the adduct to recover high purity 9,9-bis-(4-hydroxphenyl)-fluorene.

It has been found that the hydrochloric acid contained in the reaction mixture can be easily distilled off together with the resulting reaction water under reduced pressure if the method described by Morgan is followed. This has the advantage that one can work under much milder conditions, and fewer undesirable by-products due to dimerization and substitution form than when working with concentrated sulfuric acid. At the same time, disadvantages can thereby be avoided which occur in the product processing and through the then occurring solvent quantities when working in the presence of sulfuric acid or of Friedel-Crafts catalysts.

As has been seen, the condensation reaction of fluorenone and phenol in the presence of hydrogen chloride proceeds with sufficient speed already at 30° C. Preferably, temperatures between 50° and 60° C. are used since in this range, there is little formation of by-products and the reaction time to complete reaction of fluorenone is acceptably short. If, as indicated in Morgan, the reagents, fluorenone and phenol, are used in the molar ratio of 1:4, the substance solidified toward the end. But if phenol is used in 6 to 8 times the molar quantity, based on fluorenone, the composition remains stirrable throughout the reaction.

After the reaction, it is possible to remove the reaction water together with dissolved hydrochloric acid by distillation under reduced pressure, but if the phenol is used in excess, this is not advisable. If it is distilled off completely, a compact mass results as a distillation residue which can no longer be processed further. It has now been found, surprisingly, that this can be avoided if after the condensation reaction and the distillation of the hydrochloric acid-containing reaction water, an alkyl or an aralkyl nitrile is added to the residual reaction mixture. The reaction product forms a crystalline adduct with the nitrile slightly soluble in phenol and can easily be separated.

After the separation of the crystals from any excess nitrile, the phenol contained in the supernatant can be separated in a manner known in itself and be recycled in the process. In this manner, the otherwise customary washing with water or steam distillation for phenol and acid separation is avoided so that the precipitation of the product as a sticky compact mass is avoided.

A further advantage is found to be that in principle except for equimolar quantities of nitrile, no additional solvent is needed for the separation of the reaction product. In a simple process step, the formed product can be separated to over 90% from the reaction mixture. If, then, the separated phenol phase is again used for the reaction, another large portion of the product not isolated in the first step can be obtained.

Suitable for the purification of the adduct is a simple crystallization from a nitrile liquid at room temperature or from a nonpolar solvent. Also, the isolation of 9,9-bis-(4-hydroxphenyl)-fluorene from the adduct is very simple. Adducts that are formed by addition of low-boiling nitriles can be dissociated by simple thermal treatment. Higher-boiling nitriles, i.e., those having a boiling point below 130° C., can be dissociated more readily and more economically by heating in the presence of water.

In the product separation as nitrile adduct, it is of great advantage that the dissociation or respectively the drying is unnecessary if 9,9-bis-(4-hydroxphenyl)-fluorene is to be used for the production of polymer materials. 9,9-bis-(4-hydroxphenyl)-fluorene is a potential allergen. In pure, dried from, it is a finely crystalline and dust creating product. The adducts, however, occur mainly as pourable non-dusting crystals which can be handled without danger. Since the nitriles are no obstacle in certain polymerization reactions, but may even serve as welcome solvents, the isolation of the pure product can be dispensed with in these cases and the adduct wetted by solvent or nitrile can even continue to be used. In reactions with epichlorohydrin, small amounts of water have no disturbing effect so that also isolated product wet with water can continue to be used.

For the separation of 9,9-bis-(4-hydroxphenyl)-fluorene from the reaction mixture, nitriles of the formula R-CN can be used wherein R is a branched or unbranched saturated alkyl, aryl, or aralkyl radical of up to 15 carbon atoms or an arylalkyl ether. Also useful are dinitriles of the formula NC—A—CN where A is a branched or unbranched saturated alkyl of 1 to 6 carbon atoms or an optionally substituted aryl. Octanoic acid nitrile, acrylic nitrile, as well as cyanoacetic acid acetic ester do not result in adducts, however.

Examples of suitable nitriles are acetonitrile, propionic acid nitrile, n-caproic acid nitrile, capric acid nitrile, palmitic acid nitrile, trimethylacetonitrile, malonic acid dinitrile, succinic acid dinitrile, glutaric acid dinitrile, adipic acid dinitrile, hexamethylene dinitrile, benzonitrile, o- and p-toluonitile, phenoxybutyric acid nitrile, anthranilic acid nitrile and beta-naphthonitrile.

Preferably, the separation is carried out with low-boiling saturated alkyl nitriles if the pure product is to be isolated. In that case, preferably acetonitrile or propionic acid nitrile is used which can be separated from the excess phenol by simple distillation.

If 9,9-bis-(4-hydroxphenyl)-fluorene is to be used for the production of polyesters, it is found advantageous to carry out the separation with the aid of high-boiling dinitriles and to use the adducts directly for the polymerization. During the reaction, the dinitriles are released from the adducts and act as solvents. Preferably used for this purpose are dinitriles with saturated, unbranched alkyl of 3 to 6 carbon atoms and most preferred is the use of adipic acid dinitrile.

To carry out the process, fluorenone and phenol are charged in to the reaction vessel e.g. in the molar ratio of 1:6, β-mercaptopropionio acid is added as catalyst in a quantity of about 0.01 mole per mole of fluorenone used. This mixture is heated to a temperature of 50° to 60° C. While stirring, dry hydrogen chloride gas is introduced in a quantity of about 0.3 to 0.45 mole per mole of fluorenone used while continuing to stir for another 2 to 6 hours. Then, at reduced pressure and at temperatures between 40° and 90° C., the reaction water formed is distilled jointly with the dissolved hydrochloric acid.

For adduct formation, the nitrile is added to the distillation residue in 2 to 5 times the molar quantity, based on fluorenone. After everything has dissolved, the mixture is cooled and the adduct precipitates as a white, crystalline substance which can be separated in a manner known in itself. With the aid of acetonitrile, the reaction product can be obtained after drying in vacuum in a single process step in a purity of about 98%. By crystallization from additional nitrile, the purity can be increased to 99.9%. If dinitriles such as adipic acid dinitrile are used for adduct formation, this adduct can be used directly for the production of polyesters without fractionation.

Alternatively, the separated adduct can be dissociated in a simple manner by suspending it with a sufficient quantity of water (about 1 liter of water per mole of fluorenone), stirring and possibly heating to a temperature up to 90° C. At room temperature, 9,9-bis-(4-hydroxphenyl)-fluorene precipitates in crystalline form and can be filtered off. After drying and recrystallizing, 9,9-bis-(4-hydroxphenyl)-fluorene is obtained in a purity of 99.7 to 99.9%.

In the following examples, there are described several preferred embodiments to illustrate the invention. However, it is to be understood that the invention is not intended to be limited to the specific embodiments.

EXAMPLE 1

Into a melt of 180 g of 9-fluorenone (1 mole), 565 g of phenol (6 moles) and 1 g of β-mercaptopropionic acid and 14 g of hydrogen chloride (0.38 mole) were introduced at 55° C. over 6 hours, with stirring and the mixture was stirred for another 2 hours at 55° C. Then, the reaction water was distilled jointly with the hydrochloric acid and the distillation residue was then dissolved in 500 ml of acetonitrile while stirring and then cooled to 0° C. A white crystalline product precipitated which was an adduct of 9,9-bis-(4-hydroxphenyl)-fluorene and acetonitrile. After filtering, the adduct was washed four times with 150 ml of acetonitrile each time to obtain the desired adduct.

EXAMPLE 2

9,9-bis-(4-hydroxphenyl)-fluorene was released from the acetonitrile adduct of Example 1 by suspending the white crystals in 1000 ml of water with stirring for about 30 minutes. Then the white, finely crystalline 9,9-bis-(4-hydroxphenyl)-fluorene was filtered off and dried to obtain 9,9-bis-(4-hydroxphenyl)-fluorene in a yield of 80% of the theory in a purity of 98%. When the separated adduct was crystallized again from acetonitrile before the isolation of the fluorene derivative, it was obtained in a purity of 99.9%.

EXAMPLE 3

9,9-bis-(4-hydroxphenyl)-fluorene was released from the acetonitrile adduct of Example I when the white crystals were dried in vacuum at 100° to 120° C. to obtain 9,9-bis-(4-hydroxphenyl)-fluorene in a yield of 80% of the theory in a purity of 98%. When the separated adduct was crystallized again from acetonitrile before the isolation of the fluorene derivative, it was obtained in a purity of 99.9%.

EXAMPLE 4

The acetonitrile was distilled from the filtrate obtained in Example 1 and to the distillation residue, 282.5 g of phenol (2 moles), 180 g of 9-fluorenone (1 mole) and 0.5 g of mercaptopropionic acid were added. Thereafter, the condensation was carried out as described in Example 1 and in the repeated product separation, residual unisolated fluorene derivative from the first reaction can be separated as well, so that the yield was increased to 88% of the theory.

EXAMPLE 5

The distillation residue of Example 1 was dissolved with 500 ml of propionitrile instead of acetonitrile while stirring and the mixture was cooled to −15° C. and precipitation occurred. The filtered adduct was washed four times with 150 ml of propionitrile each time.

EXAMPLE 6

As described in Example 2, the propionitrile adduct of Example 5 was treated to obtain 9,9-bis-(4-hydroxphenyl)-fluorene in 70% yield of the theory in a purity of 98%. If before the isolation, the adduct was crystallized again from propionitrile, a 99.7% pure product was obtained.

EXAMPLE 7

9,9-bis-(4-hydroxphenyl)-fluorene was released from the propionitrile adduct of Example 5 and the resulting white crystals were dried in vacuum at 100° to 120° C. to obtain 9,9-bis-(4-hydroxphenyl)-fluorene in a yield of 70% of the theory and a purity of 98%.

EXAMPLE 8

Into a melt of 180 g of 9-fluorenone (1 mole), 565 g of phenol (6 moles), 1 g of β-mercaptopropionic acid and 14 g of hydrogen chloride (0.38 mole) were introduced at 55° C. over 6 hours, with stirring and the mixture was stirred for another 2 hours at 55° C. Then, the reaction water was distilled off together with the hydrochloric acid and the distillation residue was dissolved in 500 ml of acetic acid with stirring. At about 100° C., 59.5 g (0.55 mole) of adipic acid dinitrile were added and the mixture was cooled to 15° C. A white crystalline product precipitated which was an adduct of 9,9-bis-(4-hydroxphenyl)-fluorene and adipic acid dinitrile in a molar ratio of 2:1. After filtering, the adduct was washed again twice with 150 ml of acetic acid and twice with 150 ml of toluene each time. After drying at 60° C. in vacuum, 350 g of the 9,9-bis-(4-hydroxphenyl)-fluorene/adipic acid dinitrile adduct were obtained which was a yield 86.5% of the theory.

EXAMPLE 9

The product of 9,9-bis-(4-hydroxphenyl)-fluorene as well as the isolation as adipic acid dinitrile adduct was prepared using the procedure of Example 8, using 500 ml of acetic acid isobutyl ester instead of 500 ml of acetic acid. The obtained solution was cooled to 0° C. and the precipitated adduct was separated and washed to obtain after drying at about 69° C. in vacuum, 340 g (84% of the theory) of adduct.

EXAMPLE 10

The production of 9,9-bis-(4-hydroxphenyl)-fluorene as well as the isolation as adipic acid dinitrile adduct was prepared using the procedure of Example 8, using instead of 500 ml of acetic acid, 500 ml of sec. butanol. The obtained solution was cooled to 18° C. and the precipitated adduct was separated, washed, and dried at about 60° C. in vacuum to obtain 365 g (90.2% of the theory) of dinitrile adduct.

EXAMPLE 11

The production of 9,9-bis-(4-hydroxphenyl)-fluorene was prepared using the procedure of Example 8. After complete reaction, 47 g of fumaric acid dinitrile were used instead of adipic acid dinitrile. After the isolation and drying, 276 g of the 9,9-bis-(4-hydroxphenyl)-fluorene/fumaric acid dinitrile adduct (2:1 mole) were obtained which is a yield of 71% of the theory.

EXAMPLE 12

The production of 9,9-bis-(4-hydroxphenyl)-fluorene was prepared using the procedure of Example 8. After complete reaction, 59 g of glutaric acid dinitrile were added instead of adipic acid dinitrile. After the isolation and drying, 288 g of the 9,9-bis-(4-hydroxphenyl)-fluorene/glutaric acid dinitrile adduct (2:1 mole) were obtained which was a 72.4% yield.

EXAMPLE 13

The production of 9,9-bis-(4-hydroxphenyl)-fluorene was prepared using the procedure of Example 8. After complete reaction, 80 g of octanoic acid dinitrile were added instead of adipic acid dinitrile. After the isolation and drying, 315 g 9,9-bis-(4-hydroxphenyl)-fluorene/octanoic acid dinitrile adduct were obtained which corresponds to a yield of 75.2% of the theory.

Various modifications of the process of the invention may be made without deporting from the spirit or scope thereof and it is to be understood that the invention is intended to be limited only as defined in the appended claims.

What we claim is:

1. In a process for the preparation of 9,9-bis-(4-hydroxphenyl)-fluorene by condensing fluorenone and phenol in a molar ratio of 1:4 to 1:8 at 30° to 90° C. in the presence of gaseous hydrogen chloride and β-mercapto-propionic acid catalyst, the improvement comprising distilling water of reaction and dissolved hydrochloric acid from the completed reaction mixture, dissolving the distillation residue in a nitrile, separating the crystallized adduct of nitrile and 9,9-bis-(4-hydroxphenyl)-fluorene from the nitrile and dissociating the adduct to recover high purity 9,9-bis-(4-hydroxphenyl)-fluorene.

2. The process of claim 1 wherein the dissociation of the adduct is effected by heat treatment.

3. The process of claim wherein the 9,9-bis-(4-hydroxphenyl)-fluorene is suspended in water to separate the nitrile and optionally heating the suspension and recovering the white, crystallizine 9,9-bis-(4-hydroxphenyl)-fluorene.

4. The process of claim 1 wherein the adduct is used in polymerization.

5. The process of claim 1 wherein the nitrile has the formula R-CN and R is selected from the group consisting of alkyl, aryl and aralkyl of up to 15 carbon atoms and aralkyl ester.

6. The process of claim 1 wherein the nitrile has the formula NC—A—CN and A is selected from the group consisting of alkyl of 1 to 6 carbon atoms and optionally substituted aryl.

7. The process of claim 1 wherein the nitrile is acetonitrile.

8. The process of claim 1 wherein the nitrile is propionic acid nitrile.

9. The process of claim 1 wherein the distillation residue is dissolved in 2 to 5 moles of the nitrile based on the fluorenone.

* * * * *